United States Patent [19]
Clawson

[11] Patent Number: 6,106,459
[45] Date of Patent: Aug. 22, 2000

[54] METHOD AND SYSTEM FOR THE ENTRY PROTOCOL OF AN EMERGENCY MEDICAL DISPATCH SYSTEM

[76] Inventor: Jeffrey J. Clawson, 4649 Farm Meadow La., Salt Lake City, Utah 84111

[21] Appl. No.: 08/828,411

[22] Filed: Mar. 28, 1997

Related U.S. Application Data

[60] Provisional application No. 60/014,741, Mar. 29, 1996, abandoned.

[51] Int. Cl.[7] .................................................. G06F 15/42
[52] U.S. Cl. ............................................................ 600/300
[58] Field of Search .................................. 600/300, 301; 128/897, 898, 903, 904, 905

[56] References Cited

U.S. PATENT DOCUMENTS

| | | | |
|---|---|---|---|
| 4,130,881 | 12/1978 | Haessler et al. | 364/900 |
| 4,237,344 | 12/1980 | Moore | 179/2 A |
| 4,290,114 | 9/1981 | Sinay | 364/900 |
| 4,489,387 | 12/1984 | Lamb et al. | 364/514 |
| 4,839,822 | 6/1989 | Dormond et al. | 364/513 |
| 4,858,121 | 8/1989 | Barber et al. | 364/406 |
| 4,945,476 | 7/1990 | Bodick et al. . | |
| 5,063,522 | 11/1991 | Winters | 395/51 |
| 5,065,315 | 11/1991 | Garcia . | |
| 5,072,383 | 12/1991 | Brimm et al. . | |
| 5,253,164 | 10/1993 | Holloway et al. | 364/406 |
| 5,255,187 | 10/1993 | Sorensen . | |
| 5,471,382 | 11/1995 | Tallman et al. | 364/406 |
| 5,513,993 | 5/1996 | Lindley et al. | 434/319 |
| 5,521,812 | 5/1996 | Feder et al. | 364/400 |
| 5,554,031 | 9/1996 | Moir et al. | 434/111 |
| 5,596,994 | 1/1997 | Bro . | |

Primary Examiner—John P. Lacyk
Assistant Examiner—Samuel Gilbert
Attorney, Agent, or Firm—Lloyd W. Sadler

[57] ABSTRACT

A method and system for receiving, processing and responding to emergency medical calls by emergency dispatchers is described. A consistent, standard and systematic process is provided which in combination with adequate training, supervision and quality assurance serves to provide a method for gathering emergency medical information, categorizing such information into various determinant levels for appropriate response, and for giving qualified emergency medical information to callers thereby permitting "zero-time" response by those at the scene. By using this invention properly a dispatcher is guided through the interrogation of callers, gathering the critical information, dispatching the appropriate mobile care rapidly when needed and giving the appropriate guidance to the caller. This invention specifically guides the dispatcher through the universal entry protocol, thereby identifying the most urgent emergencies.

14 Claims, 5 Drawing Sheets

Microfiche Appendix Included
(1 Microfiche, 20 Pages)

ADVANCED MEDICAL PRIORITY DISPATCH SYSTEM v10.2 NAE

THE FOUR COMMANDMENTS — CASE ENTRY PROTOCOL

| Key Questions | V | Answer Choices |
|---|---|---|
| 1. What is the exact location of the incident? | ✓ | |
| 2. What is the phone number you are calling from? | ✓ | |
| 3. What's the problem (Tell me exactly what happened)? | | *(If traffic accident)* Go directly to Protocol 29 after determining number of patients (next) |
| 4. *(If not obvious)* How many people are hurt (sick)? | | |
| 5. How old is the patient? | | *(If unsure)* Obtain approximate age |
| 6. Is s/he conscious? | | Yes / No / Unknown |
| 7. Is s/he breathing? | ✓ | Yes / No → Send maximal response immediately / Uncertain (2nd party caller) / Unknown (3rd or 4th party caller) |
| 8. *(If not obvious)* Is the patient male or female? | | Male / Female |

---

CLASSIFICATIONS – TYPES – CAUSES

**Chief Complaint, *Definition***
The reason the patient is seeking medical care (in some cases only the mechanism of injury). It must contain sufficient information to allow categorization in one of the 32 defined Chief Complaints.

**Dispatch Life Support (DLS), *Definition***
The knowledge, procedures, and skills used by trained EMDs in providing care through Pre-Arrival Instructions to callers. It consists of those BLS and ALS principles which are appropriate to application by medical dispatchers.

**Verification, *Definition***
The verification column ("V") on Case Entry is provided to prompt the EMD to always verify the answers indicated ("✓").

DEFINITIONS – AXIOMS – RULES – LAWS

**Four Commandments, *Definition***
Chief Complaint, age, status of consciousness and breathing. This essential information represents the EMD's equivalent of the vital signs in traditional medicine. They are to be asked, and the answer relayed to responding units, without exception.

**Caller Party, *Definition***
1st Party: The caller is also the patient or victim.
2nd Party: The caller is in close proximity to the patient.
3rd Party: The caller is removed from, or not in close proximity to, the patient.

**Patient Age, *Category***
Infant (< 1 year)   Child (1-7 years)   Adult (≥ 8 years)

Axioms

1. The information determined for all Chief Complaints (for all cards and problems) should always include the number of people involved (or hurt) whenever it is appropriate.
2. Uncertain breathing status indicates a 2nd party caller who has seen the patient and is still unsure. This is considered not breathing until proven otherwise.
3. Unknown breathing status indicates a 3rd or 4th party caller who cannot personally verify the patient's status.

Rules

1. If patient is not breathing, a maximal response is sent immediately.
2. If patient is unconscious and breathing cannot be verified (by 2nd party caller), a maximal response is sent immediately. Then turn to the indicated DLS protocol to verify the need and provide appropriate Pre-Arrival Instructions.
3. If the Chief Complaint and status of consciousness and breathing are unknown initially (by 3rd party caller), turn to the "Unknown Problem" protocol.
4. If Traffic Accident, determine the number of patients then go directly to Protocol 29. Traffic Accidents.
5. The patient's age does not formally need to be determined initially in traffic accidents (and other multiple patient events). If individual patient assessment is possible, age should be determined at that time.
6. If conscious and breathing, go to the specific priority card, ask all Key Questions, then send the appropriate response.

FIG. 7

METHOD AND SYSTEM FOR THE ENTRY PROTOCOL OF AN EMERGENCY MEDICAL DISPATCH SYSTEM

Be it know that Jeffrey J. Clawson, a citizen of the United States of America, has invented a new and useful invention entitled METHOD AND SYSTEM FOR THE ENTRY PROTOCOL OF AN EMERGENCY MEDICAL DISPATCH SYSTEM of which the following comprises a complete specification. This application is based on Provisional Application Ser. No. 60/014,741, which was filed on Mar. 29, 1996, now abandoned and priority is claimed thereto.

BACKGROUND OF THE INVENTION

1. Field of the Invention

This invention relates to methods and systems for processing and responding to emergency medical inquiries. Specifically, this invention relates to the process or method for receiving and processing critical information regarding emergency medical calls. Also, this invention specifically relates to a system and apparatus for performing the steps of a process for receiving and processing critical emergency medical information.

Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing a consistent and proven system for: First, gathering necessary medical complaint information from emergency medical inquiry callers. Second, prioritizing the complaint to determine the criticality of the emergency. Third, providing emergency verbal instructions to individuals at the scene. Fourth, assisting dispatched responders to be prepared for each emergency situation. And, fifth, advising those on the way to provide care at the scene of specific problems or potential hazards. When used correctly this invention decreases the effective response time, while increasing the professionalism and control of emergency medical dispatchers; increases the accuracy and appropriateness of patient interrogation and well as the quality of gathered information; reduces the number of multiple unit and light-and-siren responses thereby reducing the risk of emergency medical vehicular collisions; improves patient care; reduces burn-out and stress of dispatchers by improving their quality of training and performance; decreases the risk of responder injury or mistake by providing responders with improved knowledge of the situation; and provides a means for continuously improving the quality of emergency medical dispatching and, as a result, emergency patient care.

2. Description of Related Art

It is desirable to provide a systematic and standardized method for responding to emergency medical requests. Although in the related art some attempt has been made to address the problem of medical care assessment, the related art does not address the specific problems of emergency dispatcher response. Rather related art approaches known to the applicant describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein MICROFICHE APPENDIX. This specification includes a Microfiche Appendix which includes 1 page of microfiche with a total of 20 frames. The microfiche appendix includes computer source code of one preferred embodiment of the invention. In other embodiments of the invention, the inventive concept may be implemented in other computer code, in computer hardware, in other circuitry, in a combination of these, or otherwise. The Microfiche Appendix is hereby incorporated by reference in its entirety and is considered to be a part of the disclosure of this specification.

SUMMARY OF THE INVENTION

It is desirable to provide a system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation.

Accordingly, it is the primary object of this invention to provide a medical dispatch system that is designed to guide the medical dispatcher through the initial interrogation, obtaining all critical patient information.

Another object of this invention is to provide a cross-referenced scripted set of instructions to be given by the dispatcher to the caller in a medical emergency situation.

It is a further object of this invention to provide a method of determining the criticality of a medical emergency and communicating such level of criticality to the response personnel.

It is a still further object of this invention to provide a method for gathering and communicating information concerning the situation at the field location to the response personnel and the emergency medical callers.

A further object of this invention is to improve the quality, efficiency and usefulness of the information received to and communicated by emergency medical dispatchers thereby improving the quality of emergency medical services provided to patient before, during and after the arrival of emergency medical technicians.

A still further object of this invention is to provide a method, system and apparatus for an improved entry protocol for emergency medical dispatchers.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provided. Each preferred embodiment incorporates the same essential method of this invention, though each has its own particular advantages.

BRIEF DESCRIPTION OF THE DRAWINGS

FIG. 7 depicts the preferred embodiment of the flip cards showing the steps of the entry protocol of the flip card deck embodiment of the invention.

DETAILED DESCRIPTION OF THE INVENTION

This invention provides a method, system and an apparatus for receiving, processing and communicating emergency medical information, enabling an assessment of the critical or "key" information by trained emergency medical dispatch personnel. When the invention is properly employed the initial interrogation of the caller or patient will provide critical patient information, such as the patient's location, the caller's phone number, a description of what happened, the number of people hurt, injured or sick, the patient's age, and the patient's status as to consciousness and breathing. This information is then immediately put to use identifying the criticality of the emergency and the appropriate medical response, as well as leading to a series of established medical instructions for the dispatcher to give to the caller.

Figure 1:
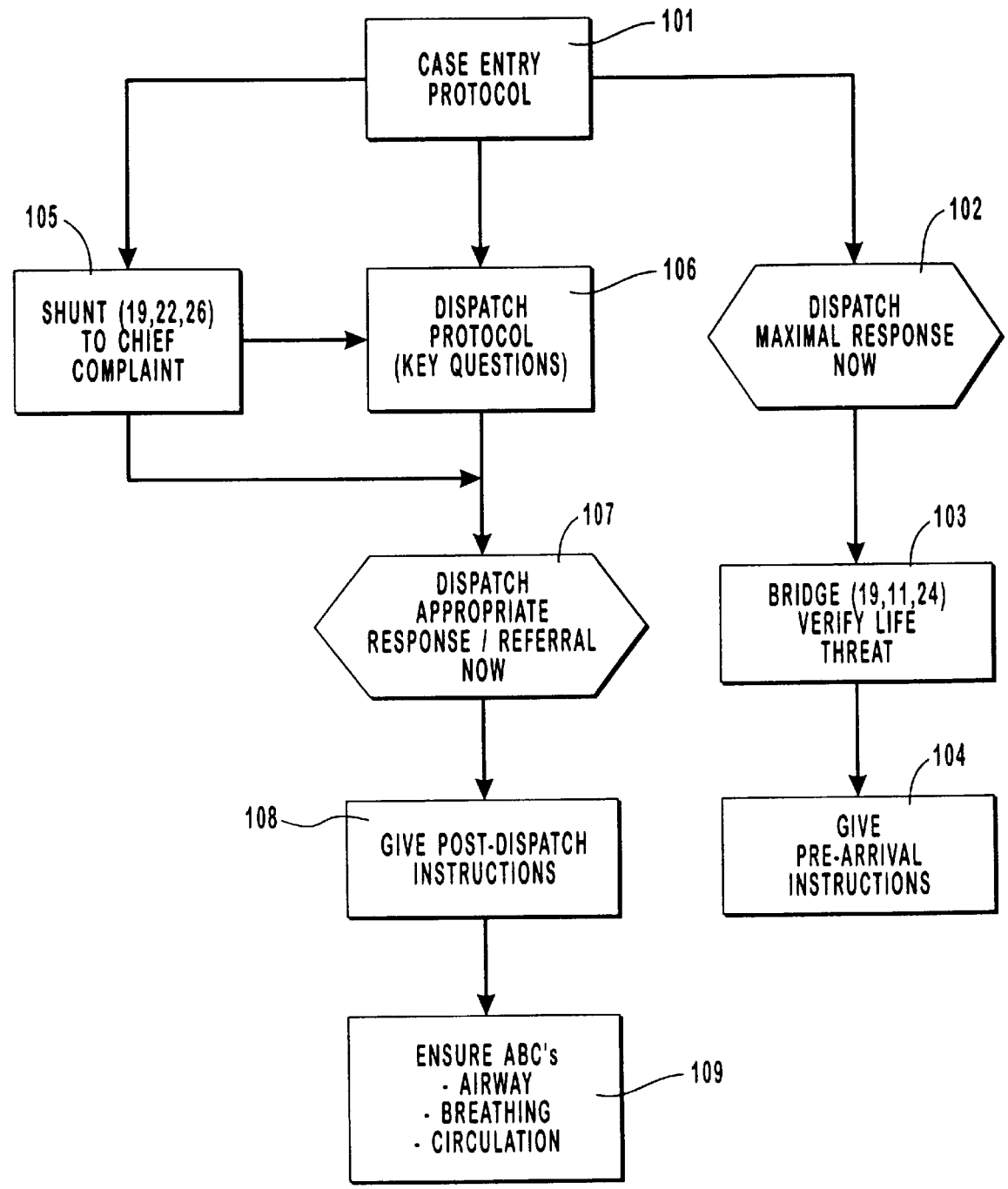
FIG. 1 depicts the principle elements of the complete system in which the preferred embodiment of the invention operates and the relationship of the elements of the system to each other and puts into the context of the complete system, the specific claimed invention.

FIG. 1 shows the complete system in which the invention operates in its best mode. The process of managing emergency medical dispatchers, the information they require and the information they give is detailed in FIG. 1. The case entry protocol 101, the heart of this invention, provides the initial steps through which the all emergency callers or patients are taken to provide symptom information and to access medical information. The purpose of the case entry protocol 101 is to receive sufficient information to permit the dispatcher to identify the caller's chief complaint. This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. The life threat is then verified 103 and pre-arrival instructions are given 104. These pre-arrival instructions 104 include six treatment sequence algorithmic scripts covering Arrest, Choking, and Childbirth. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha—A, Bravo—B, Charlie—C, and Delta—D) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
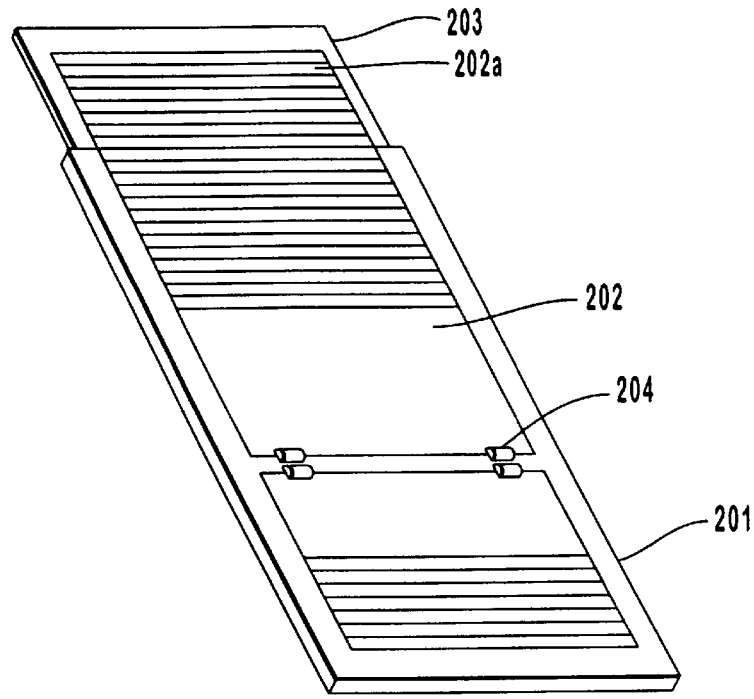
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202*a*. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
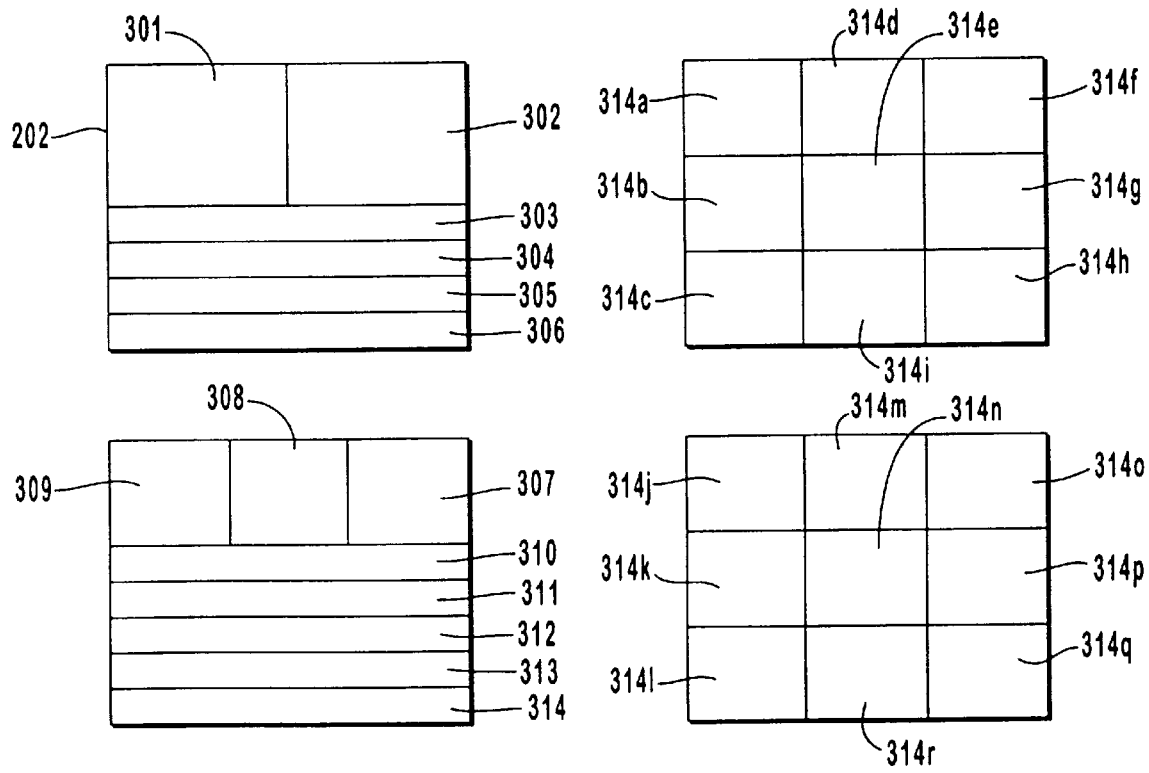
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A—Alpha 303, B—Bravo 304, C—Charlie 305 and D—Delta 306 are provided to aid the dispatcher in making the determinant designation. Each determinant level may have one or more sublevels. Generally, the most critical call is given a determinant level of D—Delta and the least critical call is given a determinant level of A—Alpha. The more critical the determinant level assigned to a call, the more medical resources and urgency may be applied to provide help. For example, an A—Alpha call will typically be responded to by emergency medical technicians and an ambulance proceeding to the patient under the safest method reasonably possible, while a D—Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene, and prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314*a–r*. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
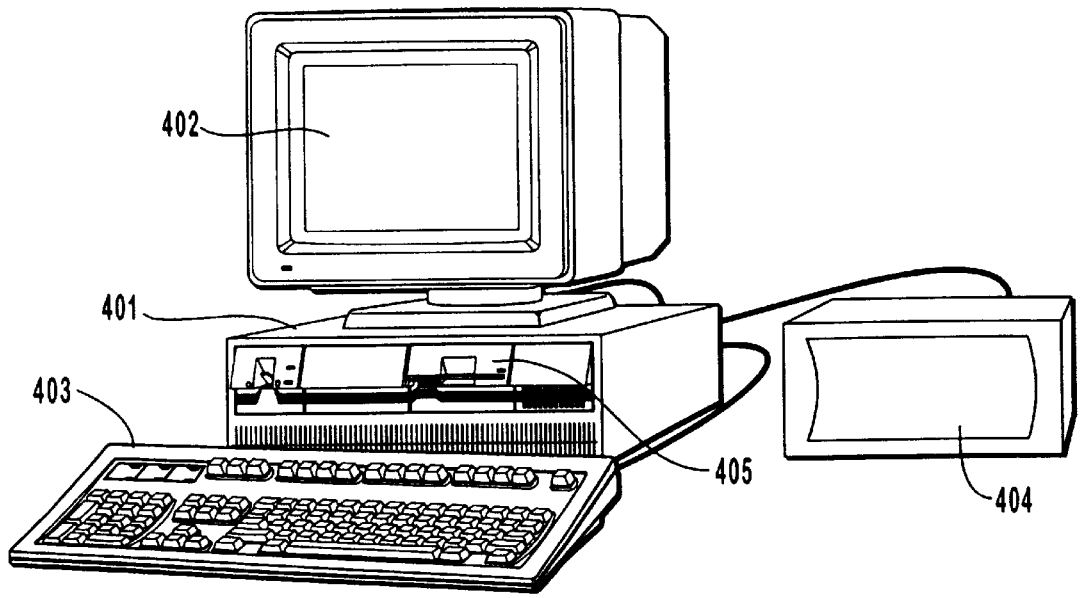
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
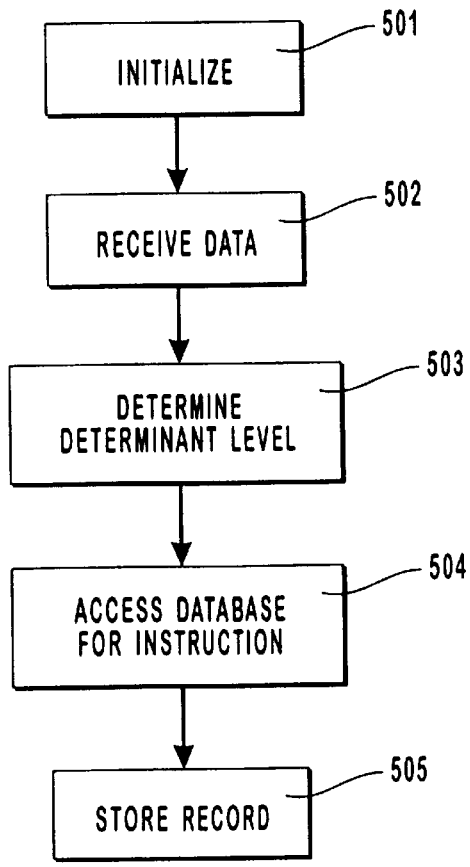
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
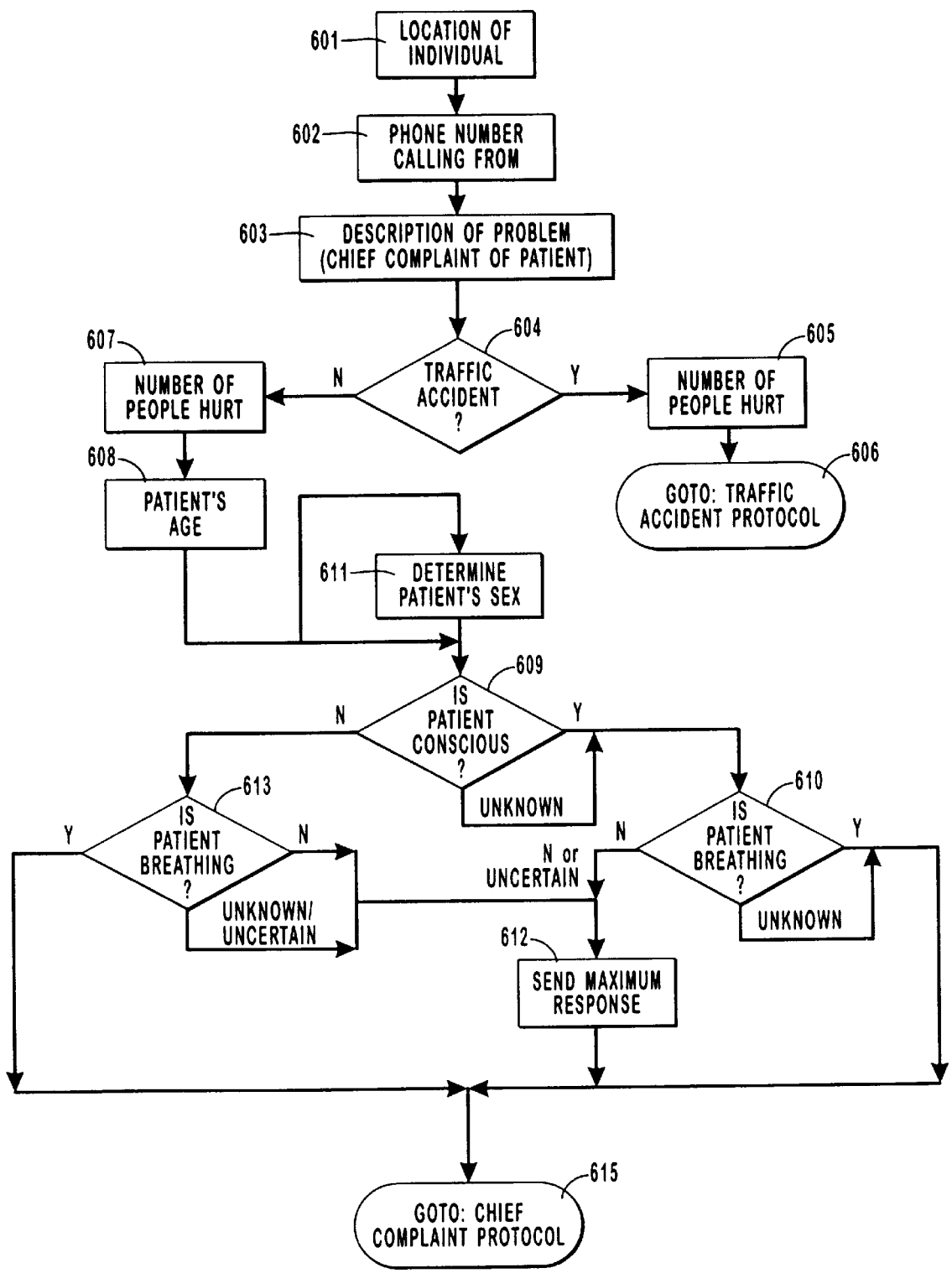
FIG. 6 depicts the detailed steps of the entry protocol steps of the process of the preferred embodiment of the invention.

FIG. 6 depicts the detailed steps of the entry protocol process of the preferred embodiment of the invention. Although the following steps of the process of the invention need not be accomplished in this specific order, alternative ordering of the steps of the invention are possible, this order of the steps of the process has been determined by the inventor to be the best mode of the invention. First, the location of the injured or ill individual (patient) is determined 601. The location is clearly essential if the dispatch of a response team is necessary. Next, the phone number where the caller is calling from is learned 602. Having the caller's phone number permits the dispatcher to call back if the call is prematurely disconnected, or if there is difficulty locating the scene or the patient. A description of the chief complaint or problem is then learned 603. The chief complaint, which is the reason the patient is seeking medical care, must contain sufficient information to allow the categorization of the problem into one of thirty-two defined chief complaints. Such categorization permits the dispatcher to branch to a protocol designed specifically to respond to the patients specific problem. If the description of the problem learned in step 603 involves a traffic accident 604, the dispatcher learns the number of people involved or injured 605 and then immediately branches to the traffic accident protocol 606. If the description of the problem does not reference a traffic accident 604 then the dispatcher inquires as to the number of people hurt 607 and then learns the patients' ages 608. The information determined for all chief complaints should always include the number of people involved or hurt, whenever it is appropriate. Such information is necessary to ensure that sufficient resources are dispatched to the scene. The patient's age is essential information as often the seriousness of an illness or injury as well as the recommended treatment depends on whether the patient is an infant (less than one year old), a child (between one and seven years old), an adult (greater than eight years old), a childbearing age female (age twelve to fifty), and/or other age/symptom categories. The key question is then asked, whether the patient is conscious 609. If the patient is either conscious or the caller is uncertain as to whether the patient is conscious then the dispatcher asks whether the patient is breathing 610. If the patient is breathing or if the caller does not know whether the patient is breathing, then the dispatcher asks if the patient is male or female, unless the problem described makes this inquiry obvious 611. However, if the patient is either not breathing 610 or is unconscious 613 and the caller is uncertain or does not know whether the patient is breathing then maximum response is dispatched 612. If the patient is breathing 613 then the dispatcher inquires as to the patients' sex, if it is not obvious from the description received as to the medical problem 614. Lastly, after the chief complaint, the patient's age, status as to consciousness and breathing are determined, the dispatcher branches to the protocol 615 most closely relevant to the description of the chief complaint.

FIG. 7 depicts the preferred embodiment of the flip cards showing the steps of the entry protocol invention. The four key questions are shown in the "Four Commandments" section 701. A "V" column 702 is provided to prompt emergency medical dispatchers to verify certain answers obtained in each and every case. An answer choice section 703 is given to prompt the dispatcher to the expected responses. Instructions for the dispatcher is given on the case entry card 704. Definitions for the chief complaint 705, the "Four Commandments" 706, dispatch life support 707, the caller party 708, and verification 709 is shown. Patient age categories are shown 710. Axioms 711 and rules 712 are provided to put the questions into context for the dispatchers.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for managing the entry process of an emergency medical dispatch system, for dispatching medical assistance to persons needing such medical assistance, comprising the steps of:

(A) receiving a medical call on a telephone communication device regarding a patient needing medical assistance;

(B) receiving a description of a problem giving rise to a call for medical assistance;

(C) receiving an age number for the person needing medical assistance;

(D) determining if the person needing medical assistance is conscious and determining if the person needing assistance is breathing;

(E) selecting an appropriate response, wherein such response depends on said described problem, said received age, said determination of consciousness and said determination of breathing (F) dispatching medical assistance to the person needing assistance based upon said selected appropriate response.

2. A method as recited in claim 1 further comprising the step of:

(e) receiving the location of the incident giving rise to said described problem.

3. A method as recited in claim 1 further comprising the step of:

(f) receiving the sex of the person needing such medical assistance.

4. A method as recited in claim 1 wherein said step of determining if the person needing assistance is conscious and determining if the person needing assistance is breathing further comprises:

(i) asking whether the person appears conscious;

(ii) asking if the person appears to be breathing; and (iii) sending a maximum medical response if the person is not certainly breathing, wherein said maximum medical response is responded to by one or more of the group consisting of emergency medical technicians, ambulance and paramedics, who proceed under the most urgent available method.

5. A method as recited in claim 1 wherein said step of receiving a description of a problem further comprises:

(i) asking for a detailed description of the medical problem;

(ii) if said problem involves a traffic accident, inquiring as to the number of people injured and selecting a traffic accident protocol for further inquiries; and (iii) if said problem does not involve a traffic accident, inquiring as to the number of people injured.

6. A system for managing the entry process of an emergency medical dispatch system, for dispatching medical assistance to persons needing such medical assistance, the system comprising:

(A) a telephone communication device for receiving a description of a medical problem, wherein such problem led to a call for medical assistance;

(B) a means for receiving the age of the person needing medical assistance;

(C) a means for identifying the state of consciousness and the state of breathing of the person needing medical assistance;

(D) a means for identifying the appropriate medical response to be given based on the description received from said first receiver, the age received from said second receiver, and the identifications made by said determiner (E) a means for dispatching medical assistance to the person needing medical assistance.

7. A system as recited in claim 6 wherein said communication device further comprises a means for receiving and processing information concerning the medical problem which led to the call for medical assistance.

8. A system as recited in claim 6 wherein said means for receiving the age of the person needing medical assistance further comprises a means for receiving and processing the age information of the person needing medical assistance.

9. A system as recited in claim 6 wherein said means for identifying the state of consciousness and the state of breathing of the person needing medical assistance further comprises a means for determining the consciousness status and breathing status of the person needing medical assistance and for dispatching emergency medical assistance if based upon said consciousness status and breathing status.

10. A system as recited in claim 6 wherein said means for identifying the appropriate medical response to be given based on the description received from said first receiver, the age received from said second receiver, and the identifications made by said determiner further comprises using the age of the person needing medical assistance in choosing the appropriate medical response to said described problem.

11. A method for managing the process for responding to an emergency medical call relating to a the entry process of a patient in a general purpose computer system comprising:

a central processing unit;

dynamic memory, static memory, a display device, an input device, an output device, a mass storage device which contains a number of emergency medical instruction records,
a number of medical information records,
a grouping of determinant codes,
a number of emergency medical inquiry reports, for managing the entry process for an emergency medical dispatching system the method comprising the steps of:

(A) selecting a type of medical problem;

(B) inputting the age of the person having said medical problem;

(C) inputting the consciousness status of the person having said medical problem;

(D) inputting the breathing status of the person having said medical problem;

(E) determining by communication over a telephone communication device whether the person having said medical problem has a breathing status of "NOT BREATHING" and if said breathing status in "NOT BREATHING" sending a maximum response dispatch; and selecting the appropriate medical response for said selected type of medical problem, said inputted age, said inputted age, said inputted state of consciousness and said inputted state of breathing of the person having said medical problem.

12. In a general purpose computer system, a method as recited in claim 11 wherein said step of determining whether the person having said medical problem has a breathing status of "NOT BREATHING" further comprises determining whether the caller is uncertain if the person having said medical problem is breathing for evaluation concerning the breathing status of the person having said medical problem.

13. In a general purpose computer system, a method as recited in claim 11 wherein said step of selecting the type of medical problem further comprises the step of determining whether the described medical problem was the result of a traffic accident.

14. In a general purpose computer system, a method as recited in claim 11 further comprising the steps of:

(g) determining the number of people needing medical assistance; and (h) determining the sex of the person needing medical assistance.

* * * * *